US00PP09516P

United States Patent [19]

Augustine

[11] Patent Number: Plant 9,516

[45] Date of Patent: Apr. 23, 1996

[54] CAESALPINIA PLANT NAMED 'DESCAP'

[75] Inventor: John R. Augustine, Phoenix, Ariz.

[73] Assignee: Desert Tree Farm, Phoenix, Ariz.

[21] Appl. No.: 388,611

[22] Filed: Feb. 14, 1995

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—Townsend and Townsend and Crew

[57] ABSTRACT

This invention relates to a new distinct variety of *Caesalpinia pulcherrima* named 'Descap'. The plant of this variety is distinguished by having flowers with the single color of yellow-orange (R.H.S. 21A). This is in contrast to the gradiated coloration of orange-red to yellow-orange (R.H.S. 33A) to R.H.S. 21A) typically found in the floral parts of *C. pulcherrima.*

1 Drawing Sheet

BACKGROUND OF THE PLANT

This *Caesalpinia pulcherrima* variety, named 'Descap' originated as a seedling at Phoenix, Ariz. 'Descap' was taken from a production block of *C. pulcherrima* of unknown parentage and maintained for asexual propagation purposes. This plant was selected from the production block because of its yellow flowers.

*C. pulcherrima* flowers normally have floral parts with a gradiated coloration of orange-red to yellow-orange (R.H.S. 33A, to R.H.S. 21A) but 'Descap' has flowers with one color, yellow-orange (R.H.S. 21A).

Asexual production of this plant was carried out at Phoenix, Ariz., by cuttings through several generations. The novel leaf color was demonstrated as firmly fixed and remaining true from generation to generation.

The following is a detailed description of my new *C. pulcherrima* plant based upon observation of plants grown at Phoenix, Ariz., the color designations being according to The R.H.S. Colour Chart published by The Royal Horticultural Society of London, England.

DESCRIPTION OF THE DRAWING

This new variety is illustrated by the accompanying photographic drawing (FIG. 1.) which shows its bloom and leaves in full color, with such colors of the photograph being as true to those of the plant as can be reasonably obtained from conventional professional photographic procedures.

DESCRIPTION OF THE PLANT

Figure 1:
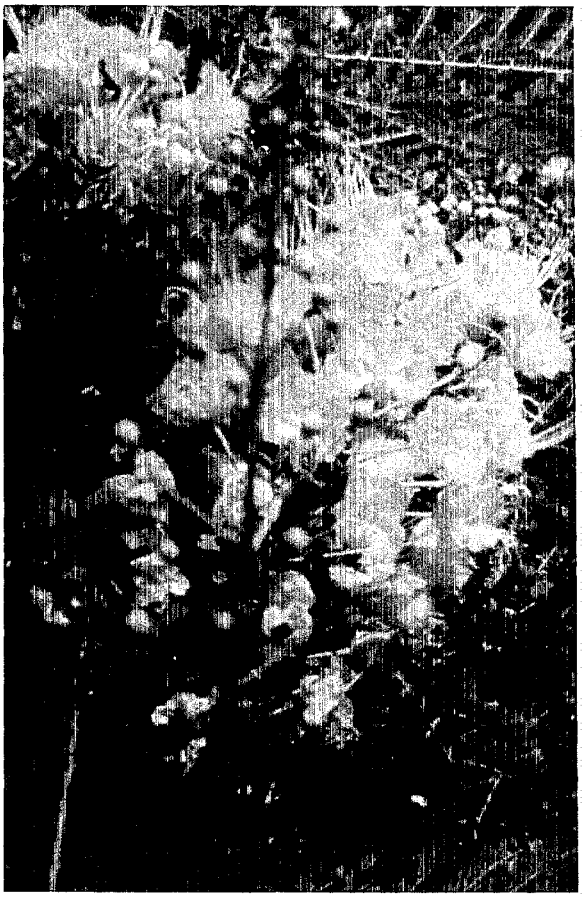

Plant form: Bush.
Plant height: To 2 m.
Plant growth habit: Perennial.
Leaf arrangement: Alternate.
Leaf type: Bipinnately compound.
Leaf rachis length: 14–20 cm long.
Leaf petiole length: 2.5–5 cm long.
Leaf petiole color: Yellow green R.H.S. 146B.
Leaf pinnae number: 14 to 20.
Leaf pinnae length: 4–8 cm long.
Leaf leaflets: 12–20 per pinna.
Leaflet shape: Oblong to oblanceolate.
Leaflet color upper: R.H.S. 147B.
Leaflet color lower: R.H.S. 194B.
Leaflet length: 7–15 mm.

Leaflet width: 5–7 mm.
Leaflet apex: Rounded to slightly emarginate.
Leaflet mucro: Weak, ca. 0.3 mm long.

DESCRIPTION OF THE FLOWER

Inflorescence type: Terminal raceme.
Inflorescence length: Up to ca. 35 cm, but with only up to about 10 cm with open flowers at a time.
Pedicel length: About 25–35 mm.
Pedical width: About 2 mm.
Flower color: Yellow orange R.H.S. 21A.
Flower number: About 10 open flowers at a time per inflorescence.
Flower shape: Zygomorphic.
Pedicel pubescence: None, glabrous.
Pedicel color: Green yellow R.H.S. 1B.
Sepal number: 5.
Upper two sepal shape: Elliptic to obovate, slightly concave.
Upper two sepal length: 10–11 mm long.
Upper two sepal width: About 6 mm.
Upper two sepal pubescence: Glabrous except for ciliate margin.
Lateral two sepal shape: Obovate, slightly concave.
Lateral two sepal length: 11–12 mm.
Lateral two sepal width: About 8 mm.
Lateral two sepal pubescence: Glabrous except for ciliate margin.
Lowest sepal shape: Obovate in outline, boat-shaped in side view.
Lowest sepal length: About 13 mm.
Lowest sepal width: About 6 mm.
Lowest sepal depth: About 5 mm.
Lowest sepal pubescence: None.
Lowest sepal margin: Denticulate, especially near apex.
Petal number: 5.
General petal shape: Obovate with an acuminate base (claw) and an expanded blade (limb).
General petal margin: With the limb irregularly crenulate, and the claw entire.
General petal pubescence: None except for minute hairs along upper surface of claw.
Upper petal claw margin: Strongly involute.
Upper petal claw length: About 10 mm.
Upper petal claw width: About 1 mm.
Upper petal limb length: About 7 mm.
Upper petal limb width: About 8 mm.

Lateral and lower petal claw margin: Slightly involute.
Lateral and lower petal claw length: About 4–5 mm.
Lateral and lower petal limb length: About 15 mm.
Lateral and lower petal limb wdith: About 15 mm.

DESCRIPTION OF THE REPRODUCTIVE ORGANS

Stamen number: 10.
Filament length: 30–45 mm.
Filament pubescence: Pubescent at base.
Filament hairs: Up to about 1 mm long.
Anther attachment: Versatile.
Anther length: About 2 mm.
Pistil number: 1.
Pistil shape: Curved upwards just above ovary.
Ovary shape: Sublinear to knife-shaped, laterally compressed.
Ovary length: About 10 mm.
Ovary width: About 2 mm.
Ovary color: Yellow Green R.H.S. 146B.
Ovary attachment: Stipitate.
Ovary stipe length: About 2 mm.
Style length: About 40 mm.
Style color: Orange yellow R.H.S. 18A.

What is claimed is:

1. The new distinct variety of *Caesalpinia pulcherrima* plant herein described and illustrated and identified by the characteristics enumerated above.

* * * * *